(12) United States Patent
Rose

(10) Patent No.: US 10,987,191 B2
(45) Date of Patent: Apr. 27, 2021

(54) TEMPLATE DEVICE FOR MARKING A SURGICAL SITE BEFORE BREAST SURGERY AND SURGICAL PROCEDURE GUIDED BY THE MARKING

(71) Applicant: Michael Rose, Herlev (DK)

(72) Inventor: Michael Rose, Herlev (DK)

( * ) Notice: Subject to any disclaimer, the term of this patent is extended or adjusted under 35 U.S.C. 154(b) by 175 days.

(21) Appl. No.: 16/413,072

(22) Filed: May 15, 2019

(65) Prior Publication Data

US 2019/0262096 A1   Aug. 29, 2019

Related U.S. Application Data

(63) Continuation-in-part of application No. 29/613,418, filed on Aug. 10, 2017, now abandoned.

(30) Foreign Application Priority Data

Feb. 10, 2017 (EM) .......................... 003746320-0001
Feb. 10, 2017 (EM) .......................... 003746320-0002
Feb. 10, 2017 (EM) .......................... 003746320-0003

(51) Int. Cl.
*A61B 90/00* (2016.01)

(52) U.S. Cl.
CPC ...... *A61B 90/39* (2016.02); *A61B 2090/3908* (2016.02); *A61B 2090/3937* (2016.02)

(58) Field of Classification Search
CPC ............ A61B 90/39; A61B 2090/3937; A61B 2090/3908; A61B 2090/395
See application file for complete search history.

(56) References Cited

U.S. PATENT DOCUMENTS

| 1,018,840 A | 2/1912 | Marikle |
|---|---|---|
| D115,118 S | 6/1939 | Lewis |
| D149,200 S | 4/1948 | Martin |

(Continued)

OTHER PUBLICATIONS

Grossmann Areola Marker Ring, no date available, [online], [site visited Aug. 13, 2018]. Retrieved from url:http://www.accuratesurgical.com/products/plastic-surgery-breast-surgery/product/2250-grossmann-areola-marker (Year: 2018), 3 pages.

(Continued)

*Primary Examiner* — Katherine H Schwiker
*Assistant Examiner* — Raihan R Khandker
(74) *Attorney, Agent, or Firm* — Ware, Fressola, Maguire & Barber LLP

(57) ABSTRACT

A triple flap nipple reconstruction is shown with preoperative incision markup lines guided by a template. The incision lines made on a patient's skin rims of flaps that are to form a reconstructed nipple. The marked-up lines define three flaps where each flap has one side in common with each of the other two flaps and also has one side in common with a part of the skin which is to be removed or de-epithelized. Also, the marked-up lines define parts of the patient's skin to be removed or de-epithelized. The surgical method thus consists of making the markup with the template with three single pedicled local dermal-fat flaps from the patient's skin and then de-epithelizing designated areas of the patient's skin, making incisions and forming, i.e., raising three flaps, forming base and elevating nipple by joining sides of de-epithelized areas, and jointing the three flaps.

7 Claims, 5 Drawing Sheets

(56) References Cited

U.S. PATENT DOCUMENTS

| | | | | |
|---|---|---|---|---|
| D157,218 S | | 2/1950 | Vanderbrook | |
| D171,246 S | | 1/1954 | Carlson | |
| 2,932,296 A | * | 4/1960 | Sanders | A61B 17/32 606/167 |
| D188,560 S | | 8/1960 | Kueter | |
| 3,037,293 A | | 6/1962 | Yost | |
| D250,094 S | | 10/1978 | Forsman et al. | |
| D252,019 S | | 6/1979 | O'Brien | |
| D270,921 S | | 10/1983 | Morgan | |
| D298,355 S | | 11/1988 | Young | |
| 5,450,751 A | | 9/1995 | Putty et al. | |
| D369,412 S | | 4/1996 | Morgan | |
| 5,618,292 A | * | 4/1997 | Poler | A61F 9/013 33/512 |
| 5,676,161 A | * | 10/1997 | Breiner | A61B 17/32053 128/898 |
| D449,338 S | | 10/2001 | Lariviere, Jr. et al. | |
| 6,686,807 B1 | | 2/2004 | Giousouf et al. | |
| 6,848,305 B2 | | 2/2005 | Fell et al. | |
| D527,659 S | | 9/2006 | Bayer et al. | |
| D527,660 S | | 9/2006 | Bayer et al. | |
| D532,324 S | | 11/2006 | Bayer et al. | |
| D548,250 S | | 8/2007 | Baumeister | |
| 7,601,080 B2 | | 10/2009 | Olson et al. | |
| D694,408 S | | 11/2013 | Matheny | |
| D715,026 S | | 10/2014 | Torres Sanchez et al. | |
| D751,151 S | | 3/2016 | Bromfield | |
| D798,451 S | | 9/2017 | Shotton et al. | |
| 2003/0051362 A1 | * | 3/2003 | Buckman | A61B 90/39 33/566 |
| 2009/0022272 A1 | * | 1/2009 | Joseph | A61B 6/469 378/37 |
| 2010/0023122 A1 | * | 1/2010 | Young | A61B 90/39 623/7 |
| 2013/0072091 A1 | | 3/2013 | Schwandner | |

OTHER PUBLICATIONS

Salz areola marker blunt, no date available, [online], [site visited Aug. 13, 2018]. Retrieved from url:https://www.gulmahersurgico.com/ solz-areola-marker-blunt-breast-reduction-surgery-stainless-steel (Year: 2018), 3 pages.

Krogsgaard et al, "Nipple Reconstruction: A Novel Triple Flap Design," Plast Reconstr Sug Open, PRS Global Open, www.PRSGlobalOpen.com, published online May 21, 2019, 6 pages.

\* cited by examiner

TEMPLATE DEVICE FOR MARKING A SURGICAL SITE BEFORE BREAST SURGERY AND SURGICAL PROCEDURE GUIDED BY THE MARKING

BACKGROUND OF THE INVENTION

The present invention relates to a template device for marking a surgical site before reconstructing of a nipple. The template makes it possible for a surgeon preoperatively to mark incision lines securing accuracy of a design needed for reconstruction of a nipple with a triple flap design. This design may improve blood perfusion of the tissue of the flaps thus improving successful healing of the reconstruction.

Reconstruction of the nipple areola complex (NAC) may be a final procedure in breast reconstructive surgery in the treatment of breast cancer. It is well known to perform nipple reconstructions by local flaps. Numerous techniques for nipple reconstructions have been described, using nipple sharing, skin grafts, and local flaps with or without augmenting material. Nipple reconstruction using single- or bi-pedicled based local flaps are the most commonly used procedures.

An often-used procedure when reconstructing nipples is to provide a single pedicled flap and reconstruct a complete nipple from this single flap by shaping the flap into a cylindric shape with a lid.

A successful healing process of a reconstructed nipple is dependent of a sufficient perfusion of blood through the tissue in the reconstruction. A flap design that improves blood perfusion will normally minimize the postoperative complication rate for nipple reconstruction.

Complication rates vary with flap design, increasing with previous radiation therapy, whereas nipple projection tends to decrease over time regardless of the surgical design.

SUMMARY OF THE INVENTION

The purpose of the present invention is to provide template and a method making it possible for a surgeon to define three flaps for reconstruction of a nipple. The template and the surgical procedure based on the template provides three flaps having a base i.e. an interface with undisturbed skin being larger than half the length l of the flap, where the length l is the distance from a base line defining undisturbed skin to the point furthest away from the base line.

According to a first aspect, the present invention relates to a template.

In accordance with the first aspect, the template is for nipple reconstruction and comprises means for marking-up incision lines on a patient's skin where the marked-up lines define rims of a flap which flap is formable into a reconstructed nipple.

In further accord with the first aspect, the marked-up lines may define three flaps where each flap has one side in common with each of the other two flaps and also has one side in common with a part of the skin which is to be removed or de-epithelized, also the marked-up lines define parts of the patient's skin to be removed or de-epithelized.

In still further accord with the first aspect, the template is constituted of a flat plate and the means for marking-up lines comprises a through-going track allowing transfer of color to the patient's skin. The plate may for example be made of a rigid material such as stainless steel or hard polymer.

According to a second aspect, the present invention relates to a surgical procedure or method for nipple reconstruction using skin and subcutaneous fat from the breast of the patient.

In further accord with the second aspect, the surgical procedure or method for nipple reconstructing is carried out using a triple flap design having three single pedicled local dermal-fat flaps, from a patient's skin comprising following:
preoperative marking of incisions using a template;
de-epithelization designated areas of the patient's skin;
incision and forming (raising) of three flaps;
forming bases and elevating a nipple by joining sides of de-epithelized areas; and
jointing the three flaps.

In still further accord with the second aspect, the areas designated for de-epithelization may be shaped as three triangles each triangle having a side or rim in common with a flap and each triangle having a corner or vertex pointing away from common side or rim and elevation of the nipple is provided through joining of the sides of the de-epithelization triangular areas.

BRIEF DESCRIPTION OF THE DRAWINGS

The accompanying drawings, forming a part thereof.

DETAILED DESCRIPTION OF INVENTION

Figure 1:
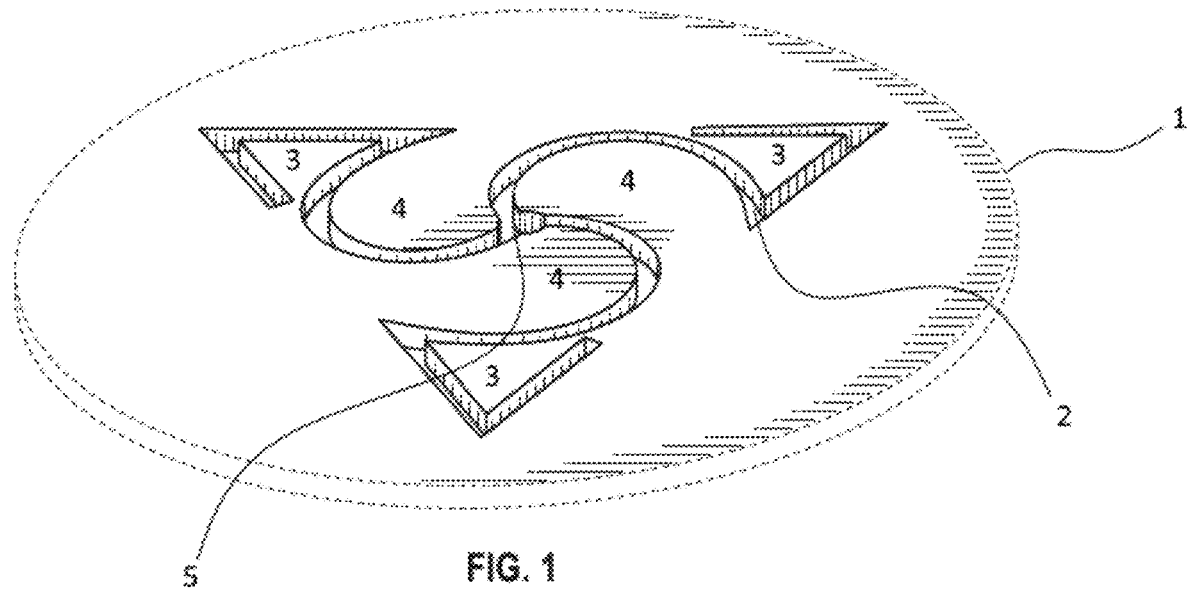
FIG. 1 is a perspective view of a first embodiment of a template device for marking of incision lines. The template has a central opening that provides a surgical guide according to the present invention as a disc template device.
Figures 2, 3:
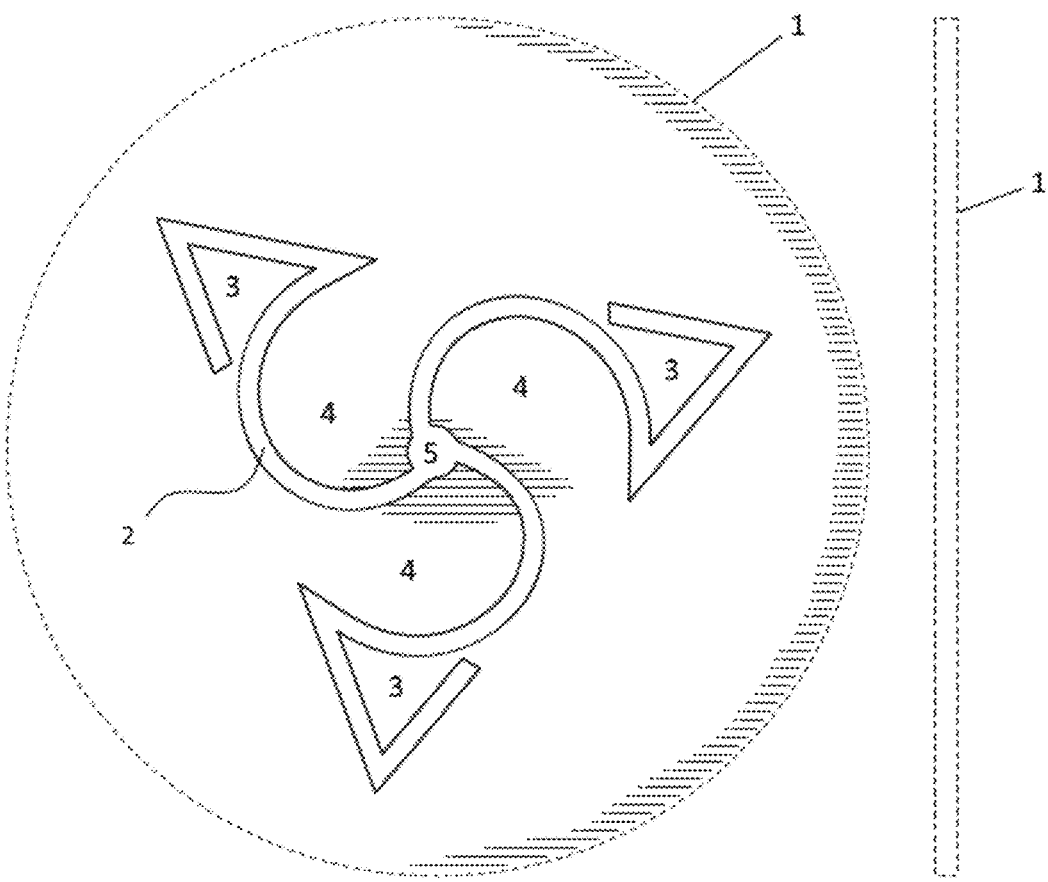
FIG. 2 is a top plan view of the template device of FIG. 1, it being understood that the bottom plan view is a mirror image of the top plan view.
FIG. 3 is a right-side view of the template device of FIG. 2, it being understood that the left side view, the front view, and the rear view are mirror images of the right-side view.
Figure 4:
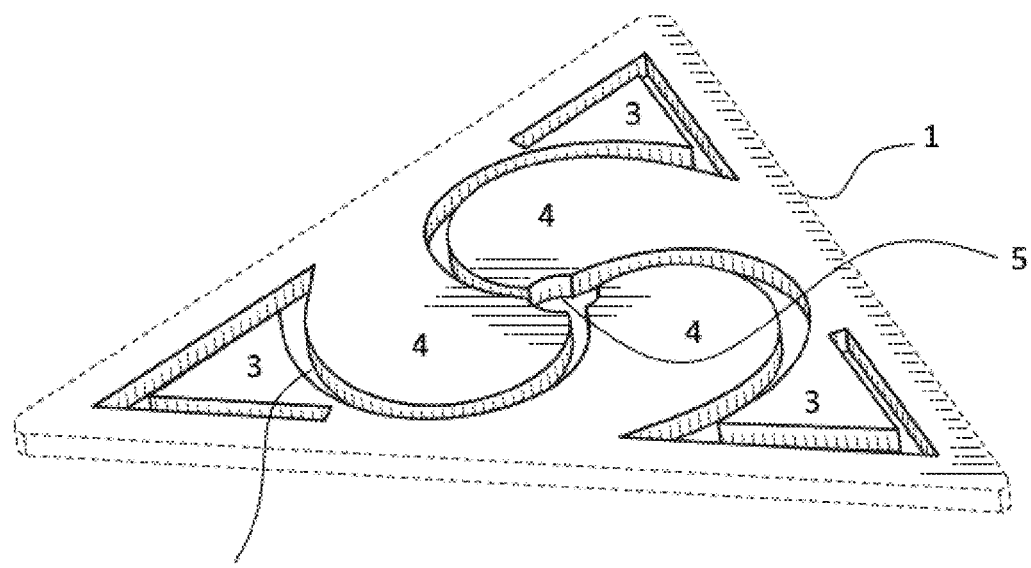
FIG. 4 is a perspective view of a second embodiment of a template device for marking of incision lines embodying the same central opening as in FIG. 1 except provided in a triangular template device.
Figures 5, 6:
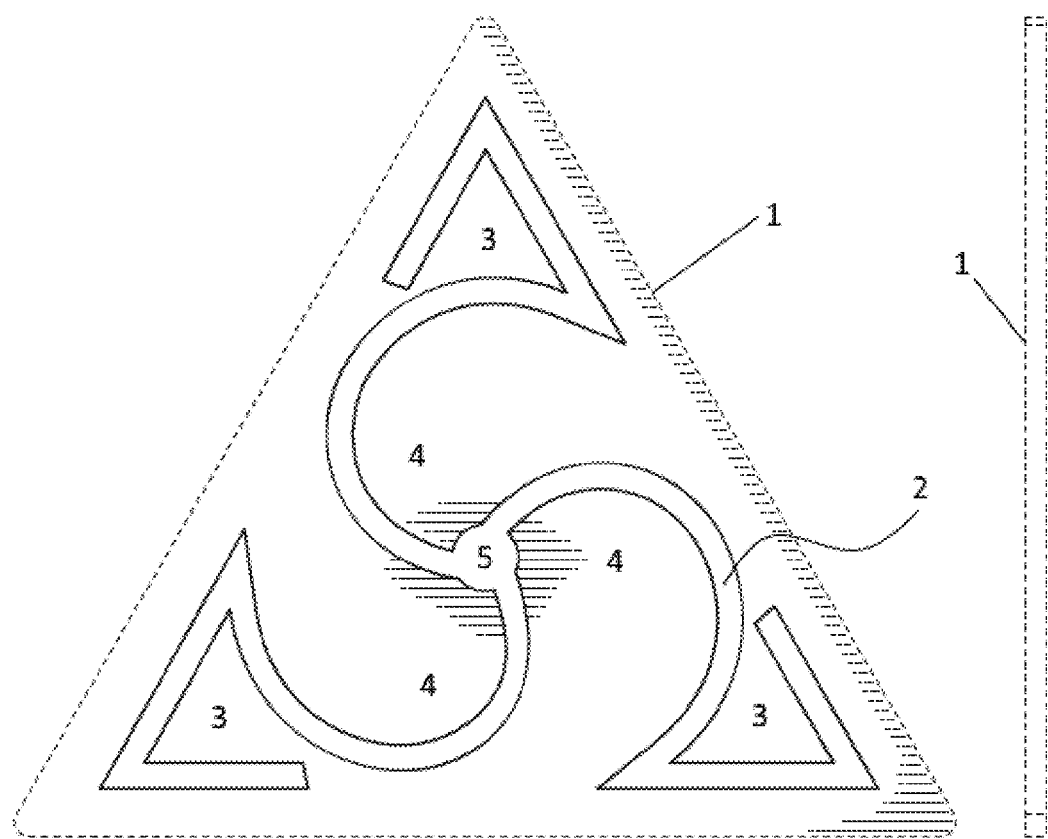
FIG. 5 is a top plan view of the template device of FIG. 4, it being understood that the bottom plan view is a mirror image of the top plan view.
FIG. 6 is a side view of one of the three sides of the template device of FIG. 5, it being understood that the other two are mirror images of the side shown.

FIGS. 1-6 show two embodiments of a template according to the invention. The template is constituted of a plate 1 of a hard or rigid material such as stainless steel or a rigid plastic material. A plastic material might be preferred if the template is disposable and designed for single use only, if the template is to be sterilized between uses, then a heat tolerant material like stainless steel is preferred. The plate 1 may have any shape e.g. round as shown in FIGS. 1-3 or triangular as shown in FIGS. 4-6.

The plate of the template 1 comprises a through-going track 2 allowing a user to draw up the pattern defined by the through-going tracks of the template 1 on the skin of a patient. In the shown embodiments, the through-going track 2 is designed as a continuous opening. It may be possible to add the pattern to the patient's skin by a stamp like device where the pattern to be transferred to the patient's skin is created by adding color such as ink to a protruding surface shaped like the pattern, and then pressing the protruding surface towards the skin. However, it might be difficult for the surgeon to position such a stamp on the exact location agreed by the patient and the surgeon. When using a template according to the invention the surgeon may place the center 5 of the template on the exact location agreed to by the patient and then draw up the remaining parts of the pattern relative to the center 5 through the through-going tracks 2 of the template.

The pattern provided by the through-going track 2 of the template defines three flaps 4 and three triangular areas 3. Each area defining a flap 4 has borders against 1) the two other flaps 4, 2) a triangular area and 3) an area where the skin of the flap is continuous with the skin of the breast or undisturbed, i.e. not incised during the procedure. When the incisions are made according to the markings each flap can be raised with a width to length ratio at 1:1.5.

Figure 7:
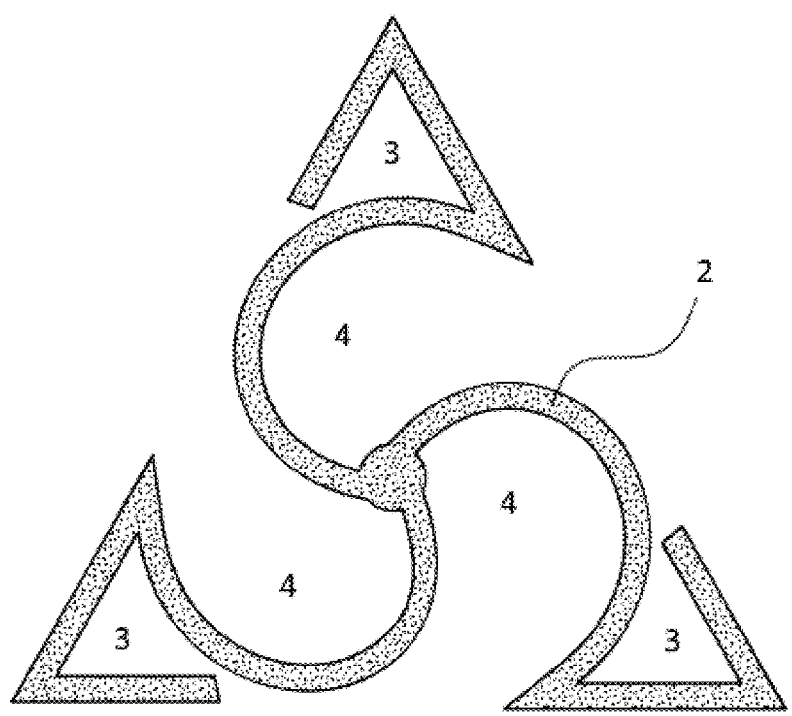
FIG. 7 shows the marking of incision lines left on the skin of the breast using a template as shown in FIG. 1-3 or FIG. 4-6. The markings may be done by drawing or in another way adding color through the openings in the template, e.g. with a pen, leaving the markings on the skin.

According to the present invention a nipple can be reconstructed by a surgical procedure or method using a triple-flap based design e.g. defined according to the above defined template:

The position of the neo-nipple is to be decided between patient and surgeon. After this, incision lines can be marked preoperatively on the breast skin, e.g. by using a template according to the invention, by adding color, e.g. by drawing, through the lines (tracks) 2 of the template thereby securing an accurate design defining exact position and size of the neo-nipple. Incisions can then be made following the markings as e.g. shown in FIG. 7.

Figure 8:
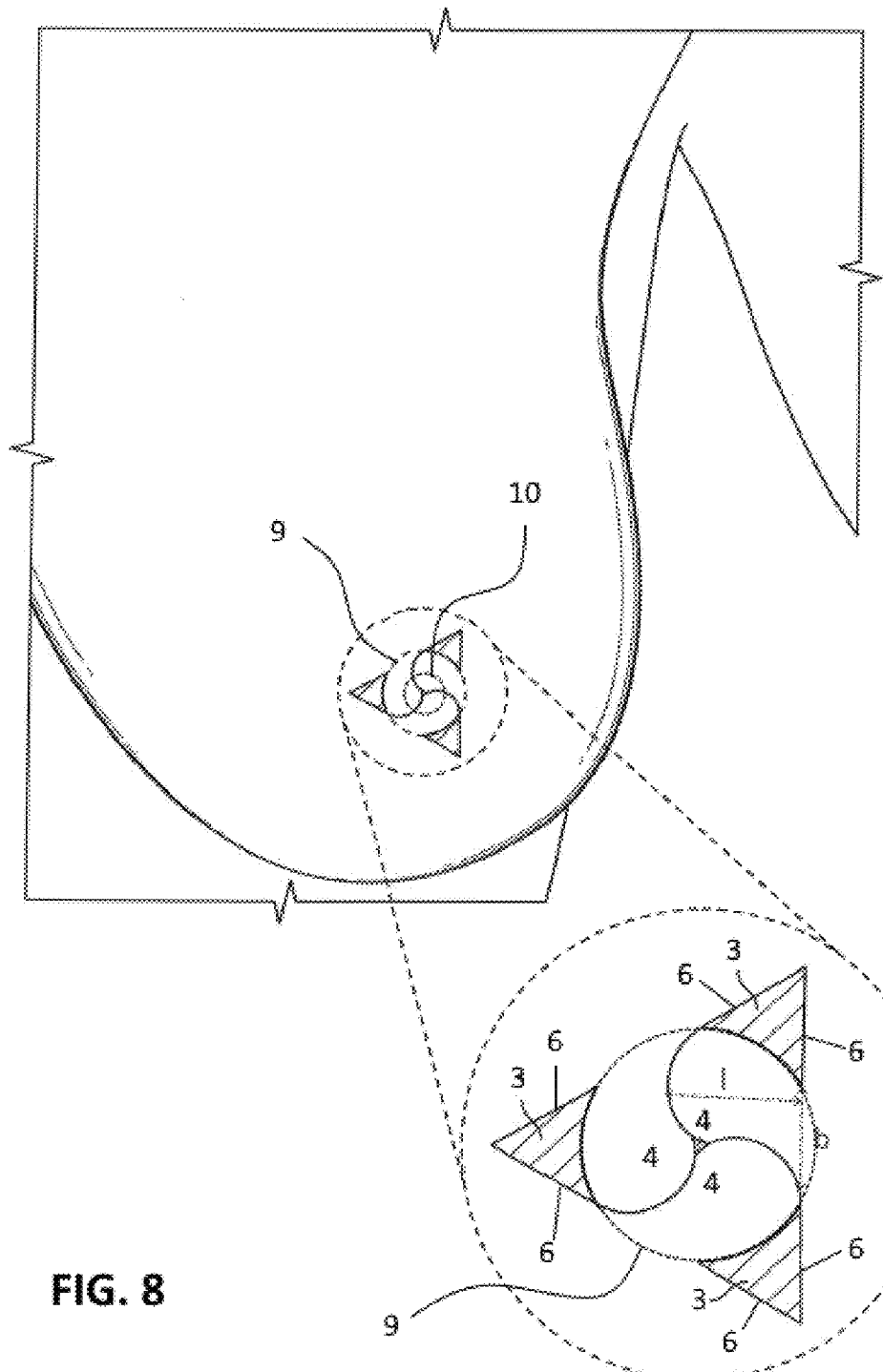
FIG. 8 shows the markings left on the skin on the breast after using a template according to FIG. 1-3 or FIG. 4-6. The shaded triangular areas are marked for de-epithelization.
Figure 9:
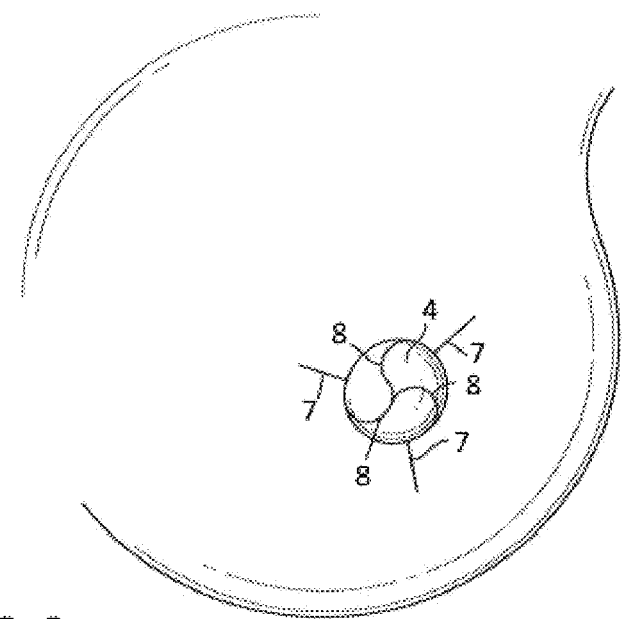
FIG. 9 shows schematically a nipple after reconstruction where the incision lines have been sutured and a new nipple has been formed from the flaps.

The three triangular areas 3 each defining a corner of the design has to be de-epithelized as illustrated in FIG. 8, and three flaps 4 comprising a suitable amount of dermal-fat can be raised with an appropriate thickness.

The side parts 6 of each of the three de-epithelized triangles are then sutured together forming three sutured lines 7 extending radially from the original border between a flap 4 and the corresponding triangular area 3. When suturing the side parts 6 of the de-epithelized triangular areas 3 together, the circumference of the skin along the border between each flap 4 and each corresponding triangular area 3 is reduced to "the foot-print" of the reconstructed nipple, causing approximation and elevation of the three flaps 4 and projection of the neo-nipple.

The reconstruction is closed by suturing corresponding sides of the raised flaps 4 e.g. by using of absorbable and non-absorbable sutures.

Tattooing of the nipple and areola area can be done approximately three months after surgery, e.g. leaving the scars within the tattooed areola.

Two dotted circles are shown in FIG. 8: an outer dotted line 9 corresponding to the base of the flaps 4 and defining the diameter of the skin before reconstruction to constitute the neo-nipple, and an inner dotted 10 line defining the diameter of the neo-nipple after reconstruction. The three equilateral triangles 3 each touch a side rim of a flap 4 along the outer dotted line 9.

The length of each base of the triangles 3 and the base of each flap 4 may constitute one-sixth of the circumference of the outer dotted line 9, where the base is the side closest to or along the outer dotted line 9. The base of each flap 4 has the length b, and the flaps' bases are thus separated from each other with one-sixth of the circumference of the outer dotted line 9. As a consequence, the ratio b:l between the width b and the length l of each flap is between 1:(1.4-1.6), and normally around 1:1.45.

Figure 10:
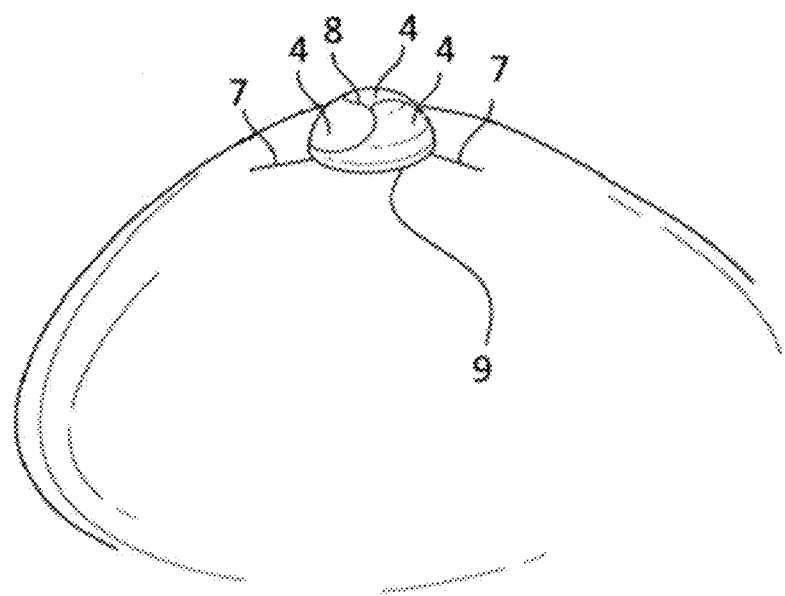
FIG. 10 shows the same reconstructed nipple as FIG. 9 seen from the side.

During operation, the bases of the triangles 3 are pulled together as the sides 6 of the triangles 3 are sutured together, this will progressively reduce the circumference of skin outside the outer dotted line 9 from the tip of the triangles 3 to the broadest part of the triangle just outside the outer dotted line 9, i.e. just outside the outer dotted line 9 the circumference will be reduced to half the size of the circumference of the original skin, and the reduced circumference will constitute the footprint of the nipple illustrated by the dotted line 10. When the sides 6 of the triangles 3 are joined, the three flaps positioned with their bases on the outer dotted line 9 will be pushed upward and forward giving rise to a cylinder-like or dome-like shape with a rounded top as illustrated in FIG. 10.

Templates for preoperative markings of the design may be made in different sizes for nipple diameters of e.g. 8, 10, 12, or 14 mm.

After reconstruction, the neo-nipple may then be dressed with a foam "chimney" bandage encircling the nipple and preventing pressure of the nipple, and covered with adhesive film for protection. Patients should not wear a bra for 2 months after operation. The bandage and sutures may be removed 10-12 days postoperatively.

| Ref. no. | Name |
| --- | --- |
| 1 | Template |
| 2 | Lines defining the incisions |
| 3 | Part defining skin removal |
| 4 | Part defining flap |
| 5 | Center of template/pattern |
| 6 | Sides of part 3 to be sutured |
| 7 | Line of sutured sides 6 |
| 8 | Line of sutured flaps |
| 9 | outer dotted line |
| 10 | Foot-print of the reconstructed nipple |
| b | Base of flap |
| l | Maximum length of flap |

The invention claimed is:

1. A template, comprising:
three identically shaped guide channels that extend from a center of the template toward an outer edge of the template, each guide channel defining an inner part and an outer part extending from the inner part, wherein
closer to the center of the template, each inner part is curved to define a side of a respective flap area, so that a total of three flap areas are defined,
wherein farther from the center of the template, the outer parts further define sides of respective triangle areas, with a base side of each respective triangle area defined by a portion of the respective inner part and with two sides of each respective triangle area opposite the respective base side defining respective triangular tops that are farthest away from the center of the template and pointing away from the center of the template toward the outer edge.

2. The template according to claim 1, wherein the template is constituted of a flat plate and the guide channels each comprise a through-going track.

3. The template according to claim 2, wherein the plate is made of a rigid material.

4. The template according to claim 3, wherein the plate is made of stainless steel.

5. The template according to claim 3, wherein the plate is made of a hard polymer.

6. A surgical method for operating on skin of a patient, comprising:
   preoperative marking of three incision lines on the skin of the patient using the template of claim 1, the incision lines designating areas on the skin of the patient;
   de-epithelizing three designated triangular areas on the skin of the patient;
   incising and forming three designated skin flap areas of the skin of the patient;
   forming a surrounding skin surface by joining sides of the de-epithelized triangular areas; and
   jointing the three designated skin flap areas to create a reconstructed nipple raised in elevation relative to the surrounding skin surface.

7. The surgical method according to claim 6, wherein each de-epithelized triangular area has a side or rim in common with a respective designated skin flap area and each de-epithelized triangular area has a pair of corner or vertex sides that together point away from the respective side or rim in common with the respective designated skin flap area and wherein elevation of the reconstructed nipple is provided through the joining of each of the pairs of the corner or vertex sides of the de-epithelized triangular areas.

* * * * *